(12) United States Patent
Badeau et al.

(10) Patent No.: US 10,564,131 B2
(45) Date of Patent: Feb. 18, 2020

(54) WATER WEDGE FOR FLEXIBLE PROBE

(71) Applicants: Nicolas Badeau, Quebec (CA); Jason Habermehl, Quebec (CA)

(72) Inventors: Nicolas Badeau, Quebec (CA); Jason Habermehl, Quebec (CA)

(73) Assignee: Olympus Scientific Solutions Americas Inc., Waltham, MA (US)

( * ) Notice: Subject to any disclaimer, the term of this patent is extended or adjusted under 35 U.S.C. 154(b) by 107 days.

(21) Appl. No.: 15/602,419

(22) Filed: May 23, 2017

(65) Prior Publication Data
US 2017/0336366 A1 Nov. 23, 2017

Related U.S. Application Data

(60) Provisional application No. 62/340,242, filed on May 23, 2016.

(51) Int. Cl.
*G01N 29/22* (2006.01)
*G01N 29/26* (2006.01)
*G01N 29/24* (2006.01)

(52) U.S. Cl.
CPC .......... *G01N 29/24* (2013.01); *G01N 29/225* (2013.01); *G01N 29/262* (2013.01); *G01N 2291/263* (2013.01)

(58) Field of Classification Search
CPC ............. G01N 29/221; G01N 29/2487; G01N 29/225; G01N 29/262; G01N 29/24; G01N 2291/02854; G01N 2291/263

USPC .......................................................... 73/644
See application file for complete search history.

(56) References Cited

U.S. PATENT DOCUMENTS

| | | | | |
|---|---|---|---|---|
| 4,200,818 A | * | 4/1980 | Ruffing | H02K 3/487 310/214 |
| 2009/0049918 A1 | * | 2/2009 | Luo | C08K 3/36 73/627 |
| 2012/0137779 A1 | * | 6/2012 | Graff | G01N 29/2487 73/632 |
| 2014/0352436 A1 | * | 12/2014 | Zhang | G01N 29/07 73/598 |
| 2015/0219602 A1 | | 8/2015 | Bond-Thorley et al. | |
| 2016/0231283 A1 | * | 8/2016 | Takemoto | G01N 29/043 |
| 2017/0074831 A1 | * | 3/2017 | Zhang | G01N 29/07 |

FOREIGN PATENT DOCUMENTS

WO 2012056218 A1 5/2012
WO 2014023938 A2 2/2014

* cited by examiner

*Primary Examiner* — Jacques M Saint Surin
(74) *Attorney, Agent, or Firm* — Gerald P. Kazanjian

(57) ABSTRACT

Disclosed is an ultrasonic inspection probe assembly comprising a water wedge and a flexible probe array assembly having a flexible acoustic module. The wedge is machined to match a test surface to be inspected and is configured to shape the acoustic module so that the active surface of the acoustic module is parallel to the test surface. Different wedges may be machined to match different test surfaces, but the same flexible probe array assembly may be used for all such surfaces.

13 Claims, 6 Drawing Sheets

WATER WEDGE FOR FLEXIBLE PROBE

CROSS-REFERENCE TO RELATED APPLICATIONS

This application claims the benefit and priority of U.S. Provisional patent application Ser. No. 62/340,242 filed May 23, 2016 entitled WATER WEDGE FOR FLEXIBLE PROBE, the entire disclosure of which is incorporated herein by reference.

FIELD OF THE INVENTION

The invention relates to water wedges and ultrasonic probe arrays used for non-destructive test and inspection (NDT/NDI).

BACKGROUND OF THE INVENTION

Performing high-resolution ultrasonic thickness mapping of complex shapes with changing geometries, such as elbows, bends, nozzles, or any part with variable geometry is very challenging. To map the thickness of such components, conventional ultrasonic probes must be held perpendicular to the surface at every point of data acquisition. This process is slow and corrosion pits can be missed between acquisition points. Using ultrasonic phased array probes allows large areas to be rapidly scanned at high-resolution, but standard linear phased array probes are rigid and cannot conform to changes in component geometry.

When performing NDT/NDI with a phased array probe, the ultrasonic focal laws must be arranged so the propagation direction of the beam is perpendicular to the test object surface. Such inspection is usually done using local immersion by means of a water wedge, in which water is used as the coupling medium between the probe and the test object. However, any other suitable coupling medium may also be used. To ensure that the propagation direction of the beam is perpendicular to the test object surface, the probe curvature must substantially match the part curvature. In existing practice a flat probe array may be used for a flat surface, whereas for a pipe a custom probe must be made for each pipe diameter, and complex custom probes must be manufactured for complex part surfaces.

Manufacture of custom wedge designs is possible at reasonable cost using standard machining or 3D printing techniques. However, design and manufacture of custom probe array geometries is only possible with long manufacturing lead times and at great expense.

US patent application 2015/0219602 discloses a wedge for a flexible ultrasonic array, in which inspection of a curved surface is done by inserting the flexible array between two detachable parts of the wedge. However the wedge, having two parts, is complex to manufacture, requires tools to disassemble and assemble, and is inconvenient and time consuming to use.

SUMMARY OF THE INVENTION

Accordingly, it is a general objective of the present disclosure to provide a solution which avoids the expense and long lead times of custom probe array designs.

It is further an objective of the present disclosure to make use of a flexible ultrasonic phased array probe having a flexible acoustic module designed for high-resolution inspection of complex shapes.

It is further an objective of the present disclosure to provide a wedge configured to shape the acoustic module so that the active surface of the acoustic module is parallel to the test surface.

It is further an objective of the present disclosure to provide a wedge comprising an integral rigid block, into which a flexible acoustic module may be slidably inserted.

It is further an objective of the present disclosure to provide a flexible ultrasonic phased array probe which may be interchanged between different water wedges, with an interchange time that is less than one minute and does not require use of any tools.

It is further an objective of the present disclosure to use the same flexible probe for a variety of part shapes, such as pipes of various diameter and other complex shapes, by employing different wedges that form the acoustic module into a shape which substantially conforms to the surface of the test object and so that the active surface is parallel to the test surface.

In an embodiment, a water wedge is provided which enables insertion of a flexible acoustic module, so that the acoustic module glides into a slot which bends the flexible module, thereby forming it into a shape which substantially conforms to the surface of a test object so that the active surface is parallel to the test surface.

DETAILED DESCRIPTION OF PREFERRED EMBODIMENT

Figure 1A:
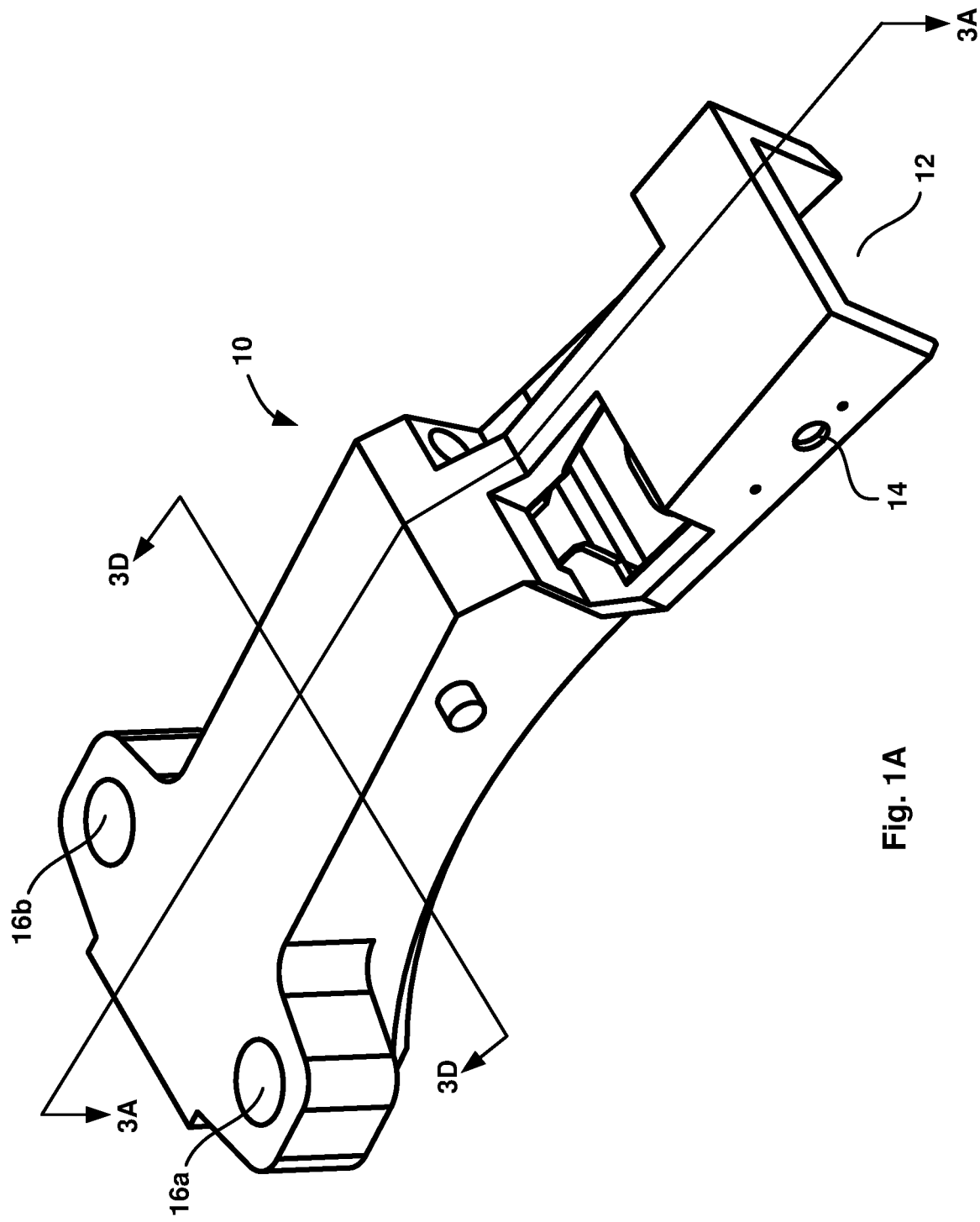
FIG. 1A is an isometric view of a water wedge according to the present disclosure.
Figure 2:
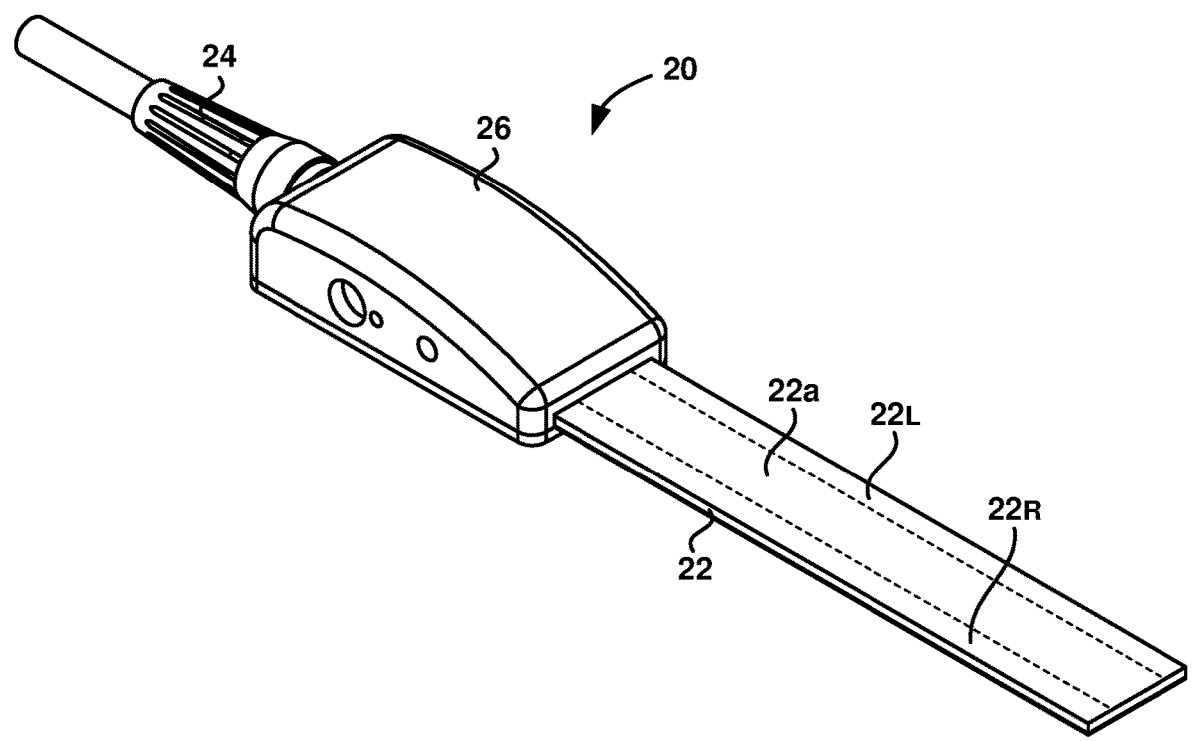
FIG. 2 is an isometric view of a flexible probe array assembly according to the present disclosure.

FIG. 1A is an isometric view of a water wedge 10, having an opening 12 for insertion of a flexible probe array 20 (see FIG. 2). An aperture 14 is configured for insertion of a screw (not shown) for tightening in order to lock flexible probe array 20 in position. Apertures 16a and 16b are configured to accept bolts (not shown) for connection to a probe scanner mechanism (also not shown).

Figure 1B:
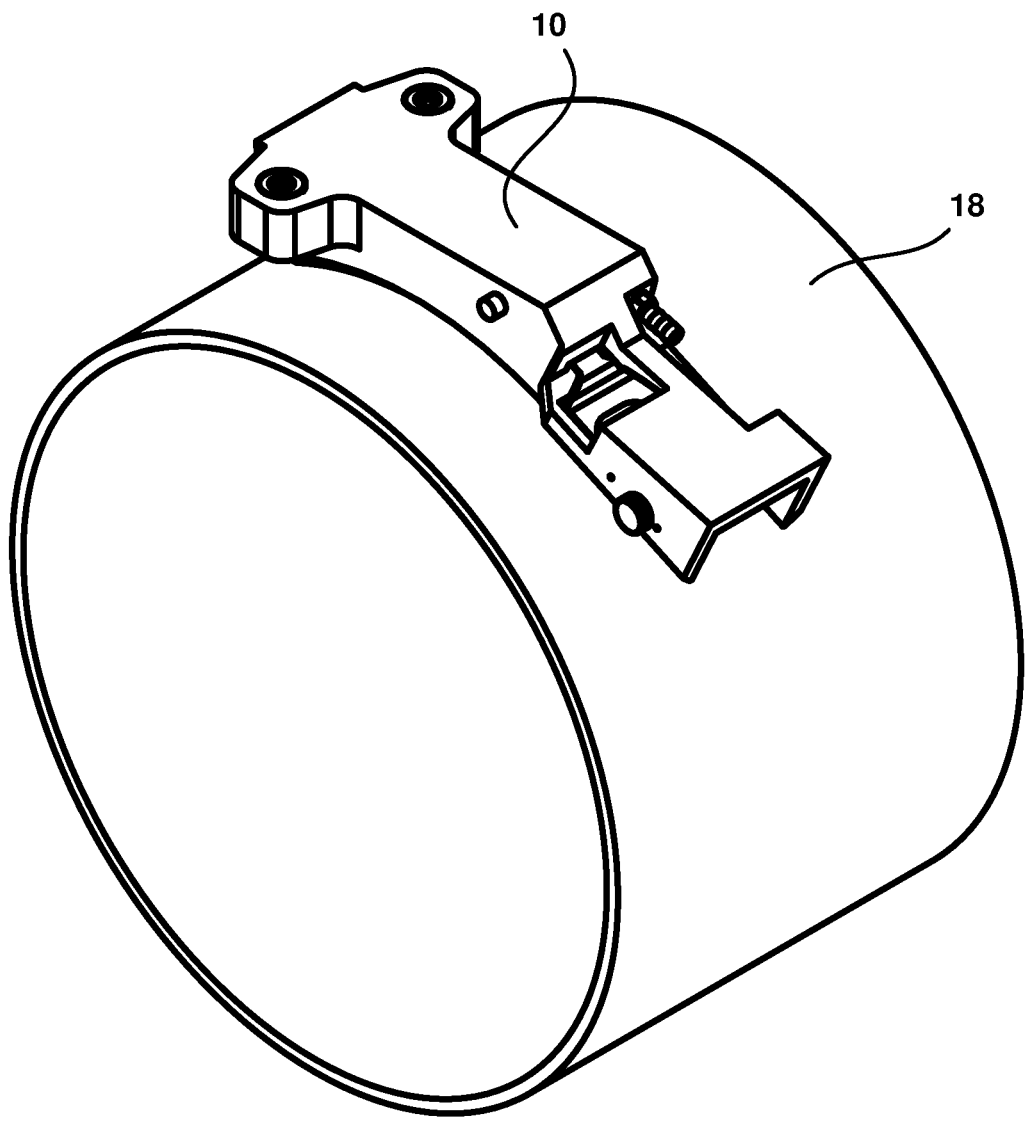
FIG. 1B is an isometric view of a water wedge according to the present disclosure in position on a pipe under inspection.

FIG. 1B shows water wedge 10 in position on a pipe 18 for making NDT/NDI measurements on pipe 18. Water wedge 10 is shown before insertion of flexible probe 20 into water wedge 10.

FIG. 2 is an isometric view of flexible probe array assembly 20, comprising a flexible acoustic module 22, a cable assembly 24 and a housing 26. Flexible acoustic module 22 comprises one or more acoustic arrays (not shown), such as piezoelectric arrays, which are configured to emit ultrasonic energy into the test object and to receive echo signals from the test object. Cable assembly 24 is configured to be connected to an acquisition unit (not shown) which controls the acoustic emission and processes the echo signals. In an embodiment, flexible acoustic module 22 is a ribbon, as shown in FIG. 2, which has an active surface 22a, a left inactive surface 22L and a right inactive surface 22R. Active surface 22a corresponds to the region of acoustic module 22 having acoustic arrays, while inactive surfaces 22L and 22R correspond to regions of acoustic module 22 where acoustic arrays are absent.

Figure 3A:
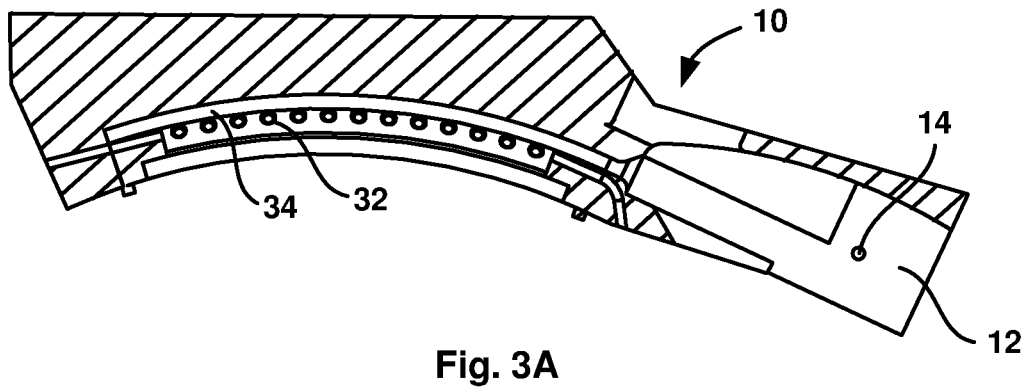
FIG. 3A is a section view of a water wedge according to the present disclosure.

FIG. 3A is a section 3A-3A of water wedge 10, showing water irrigation channels 32, and a slot 34 having module positioning tracks (see FIG. 3D) for slidably inserting flexible probe array 20. A water seal (not shown) confines a water column between water wedge 10 and the surface of the test object. In an embodiment the water column height is 8 mm. However, any water column height may be used and all are within the scope of the present disclosure.

Figure 3B:
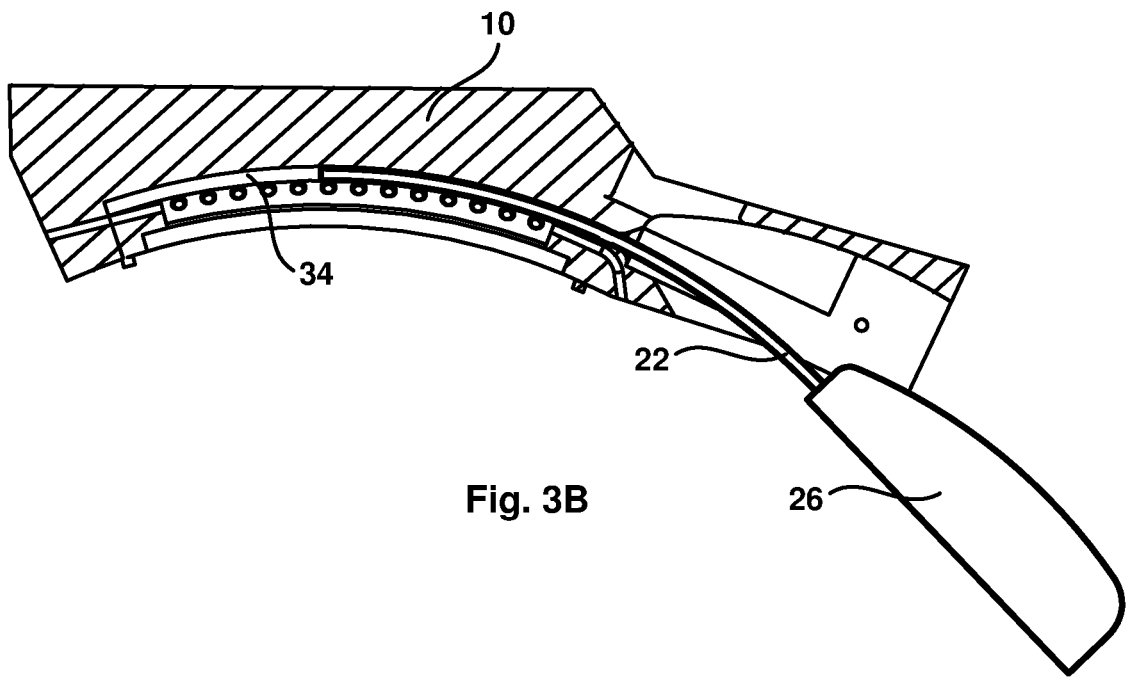
FIG. 3B is a section view of a water wedge with partially inserted flexible probe array assembly.

FIG. 3B shows the same section of wedge 10 as in FIG. 3A, together with flexible probe array 20 which is partially inserted, so that flexible acoustic module 22 is being slidably shaped by slot 34 while housing 26 still remains outside wedge 10.

Figure 3C:
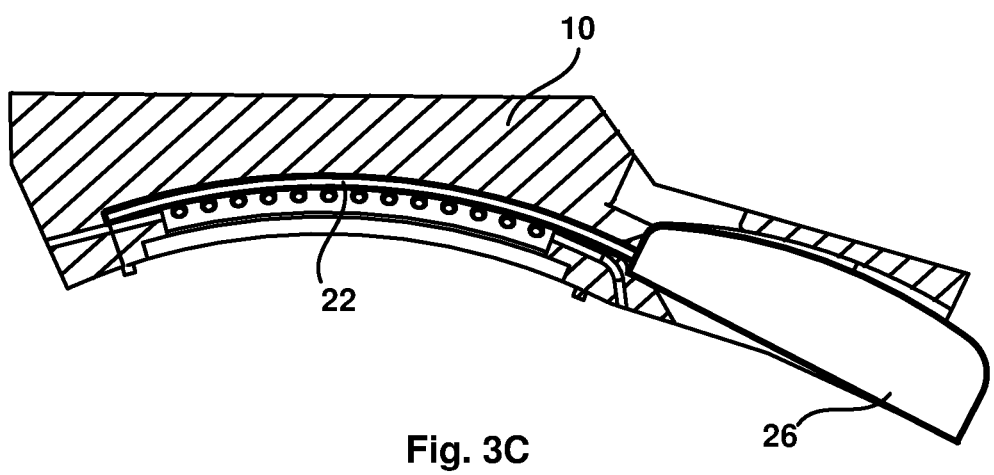
FIG. 3C is a section view of a water wedge with fully inserted flexible probe array assembly.

FIG. 3C shows the same section of wedge 10 with flexible probe array 20 fully inserted. Flexible acoustic module 22 fully occupies slot 34 and conforms to its shape. Housing 26 is contained within opening 12 and is locked into position by a screw inserted into aperture 14.

Figure 3D:
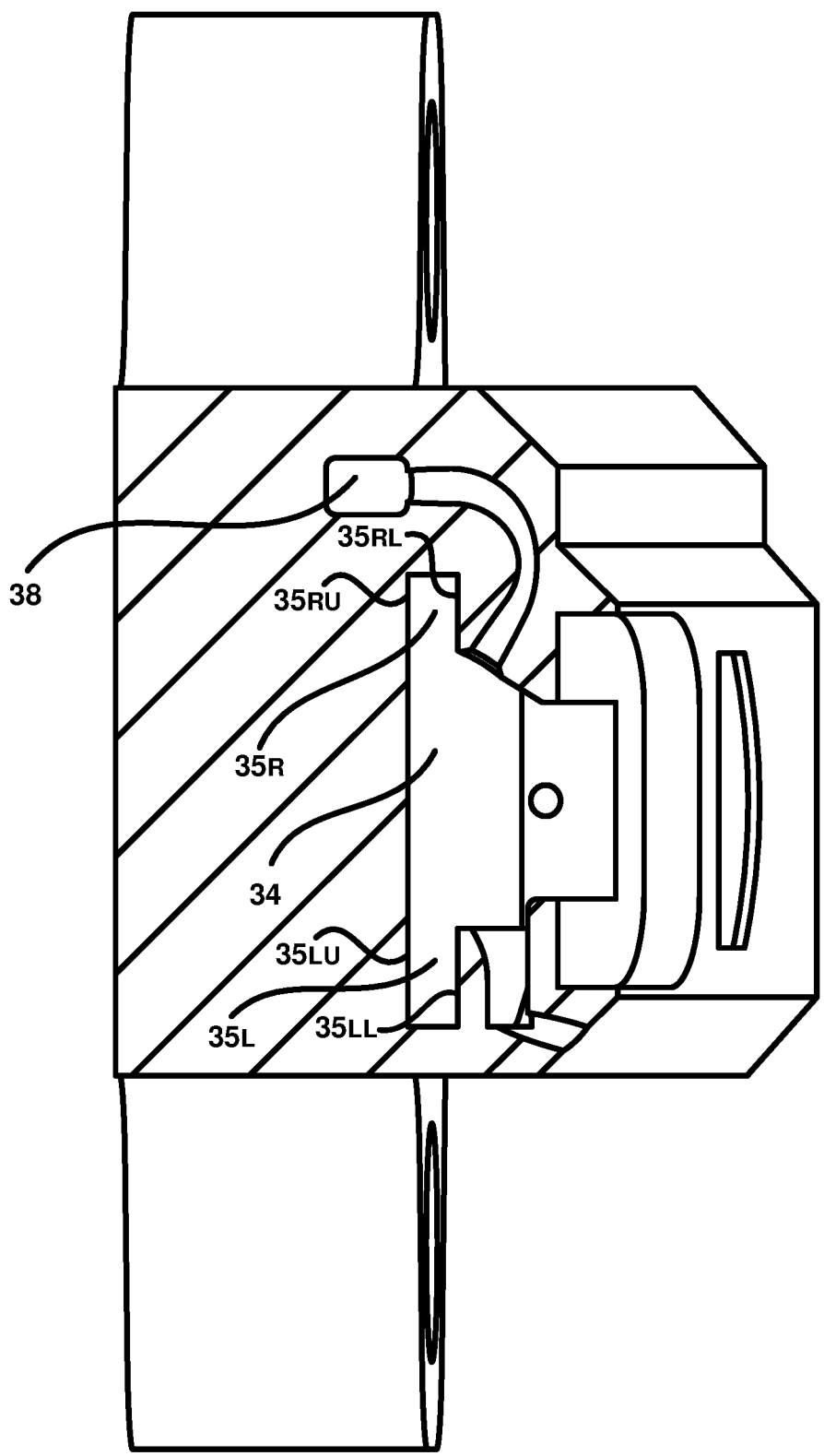
FIG. 3D is a sectional end view of a water wedge showing a slot for insertion of a flexible probe array.

FIG. 3D is an end view section 3B-3B of wedge 10, showing that slot 34 has a left module positioning track 35L and a right module positioning track 35R. Left track 35L has a left upper shaping surface 35LU and a left lower shaping surface 35LL, and right track 35R has a right upper shaping surface 35RU and a right lower shaping surface 35RL. Note that surfaces 35LU, 35LL, 35RU and 35RL are machined to be parallel to the test surface of the object to be inspected. Note also that custom versions of wedge 10 may be machined to so that surfaces 35LU, 35LL, 35RU and 35RL conform to specific test object surfaces, and that slot 34 is configured to accept insertion of flexible acoustic module 22 irrespective of the shapes of surfaces 35LU, 35LL, 35RU and 35RL.

Module positioning tracks 35R and 35L ensure that flexible acoustic module 22 is captured within slot 34 and that flexible acoustic module 22 is thereby forced to conform to the shape of surfaces 35LU, 35LL, 35RU and 35RL as flexible module 22 is slidably inserted. This is achieved by capturing right inactive surface 22R between surfaces 35RU and 35RL, and capturing left inactive surface 22L between surfaces 35LU and 35LL.

FIG. 3D also shows a water manifold 38 for provision of water to irrigation channels 32.

Figure 4A:
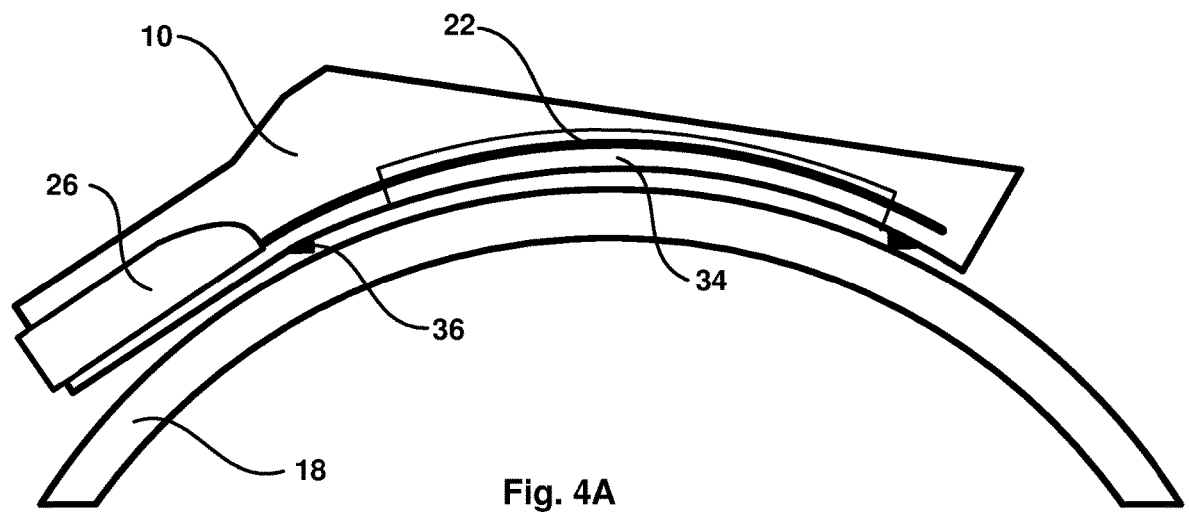
FIG. 4A is a schematic of a water wedge with inserted flexible probe, in position to measure a circular pipe.
Figure 4B:
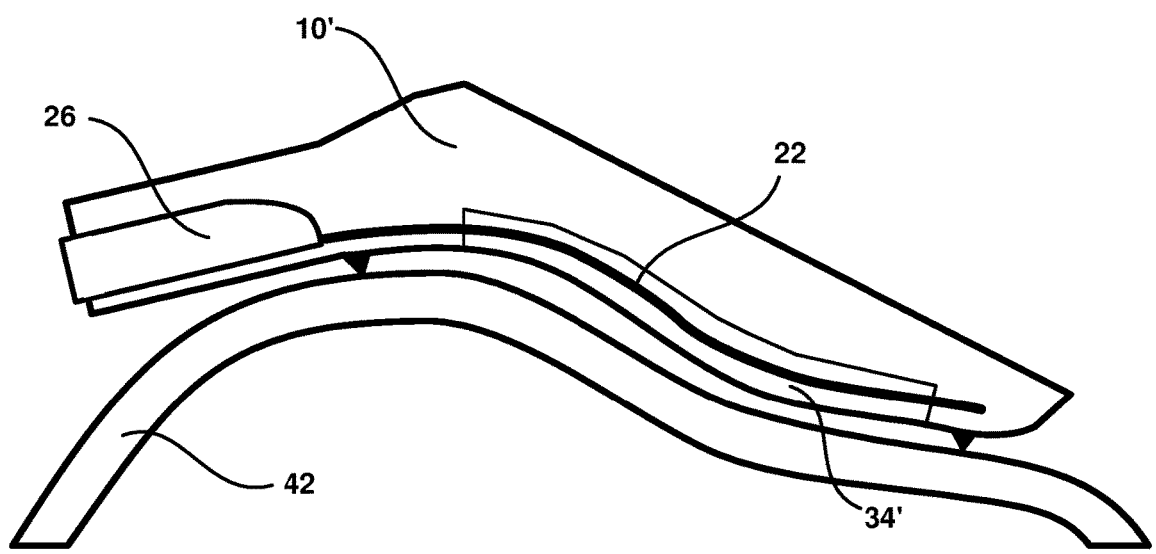
FIG. 4B is a schematic of a water wedge with inserted flexible probe, in position to measure a complex surface.

FIG. 4A is a schematic showing flexible acoustic module 22 and housing 26 inserted into slot 34 of wedge 10 for inspection of circular pipe 18. FIG. 4B is a schematic showing the same flexible acoustic module 22 and the same housing 26 inserted into a different slot 34' of a different wedge 10' for inspection of a complex test object 42.

Note that wedge 10 as herein illustrated and described is an embodiment of a wedge comprising a single rigid block and having a slot configured to form an acoustic module shape, wherein the acoustic module shape is a shape of the acoustic module such that the active surface is substantially parallel to the test surface. Other embodiments of wedges configured to form the acoustic module shape may be devised. For example, the acoustic module may have a central inactive surface and may be slidably inserted into a slot having upper and lower module positioning tracks above and below the central inactive surface.

Although the present invention has been described in relation to particular embodiments thereof, it can be appreciated that various designs can be conceived based on the teachings of the present disclosure, and all are within the scope of the present disclosure.

What is claimed is:

1. An ultrasonic inspection probe assembly for inspecting a test object, the test object having a test surface with a test surface shape, the probe assembly comprising:
    an array probe comprising an acoustic module having an external shape and an active surface configured to emit ultrasonic energy into the test object and to receive echo signals from the test object; and,
    a wedge comprising an integral rigid block configured with one surface to be placed in contact with the test surface, the wedge having a slot configured to have a shape corresponding to the test surface shape and to substantially enclose the acoustic module; and,
    wherein the acoustic module is slidably inserted into the slot such that the active surface is substantially parallel to the test surface.

2. The inspection probe assembly of claim 1 wherein there is a gap between the active surface and the test surface, the gap having a substantially constant thickness perpendicular to the test surface, the gap being filled with an acoustic couplant, the acoustic couplant facilitating transmission of ultrasonic energy from the active surface to the test surface.

3. The inspection probe assembly of claim 1, wherein the array probe is a flexible probe and the acoustic module is bendable along a longitudinal direction.

4. The inspection probe assembly of claim 1 wherein the slot comprises one or more shaping surfaces, wherein the shaping surfaces are substantially parallel to the test surface.

5. The inspection probe assembly of claim 1 wherein manufacture of the acoustic module is independent of the test surface shape.

6. The inspection probe assembly of claim 3 wherein the acoustic module is a module ribbon having a module width, and the active surface is an active ribbon having an active width, the active width being less than the module width, and wherein the module ribbon has a left inactive ribbon surface and a right inactive ribbon surface.

7. The inspection probe assembly of claim 6 wherein the slot has a left module positioning track and a right module positioning track, wherein the left track has a left upper shaping surface and a left lower shaping surface and the right track has a right upper shaping surface and a right lower shaping surface, and wherein the left upper shaping surface, the left lower shaping surface, the right upper shaping surface and the right lower shaping surface are substantially parallel to the test surface.

8. The inspection probe assembly of claim 7 wherein the acoustic module is slidably inserted into the slot such that the left inactive ribbon surface is between the left upper shaping surface and the left lower shaping surface, and the right inactive ribbon surface is between the right upper shaping surface and the right lower shaping surface.

9. The inspection probe assembly of claim 2 wherein the acoustic couplant is water.

10. The inspection probe assembly of claim 9 wherein the wedge further comprises a water manifold for introduction of the acoustic couplant.

11. The inspection probe assembly of claim 9 wherein the wedge further comprises at least one water seal configured to confine the acoustic couplant between the active surface and the test surface.

12. The inspection probe assembly of claim 1 wherein the test surface shape is cylindrical.

13. The inspection probe assembly of claim 1 wherein the test surface shape is a complex shape.

* * * * *